United States Patent [19]

Eggenschwiler

[11] Patent Number: 5,302,815
[45] Date of Patent: Apr. 12, 1994

[54] LIGHT PROTECTION APPARATUS COMPRISING AN ELECTRICALLY CONTROLLABLE LIGHT PROTECTION FILTER ELEMENT

[75] Inventor: André M. Eggenschwiler, Stäfa, Switzerland

[73] Assignee: Optrell AG, Wattwill, Switzerland

[21] Appl. No.: 936,900

[22] Filed: Aug. 27, 1992

[30] Foreign Application Priority Data

Jan. 10, 1992 [CH] Switzerland ............................ 57/92

[51] Int. Cl.⁵ .......................... G02F 1/13; A61F 9/06
[52] U.S. Cl. .................. 250/201.1; 250/205; 2/8; 359/66
[58] Field of Search ............. 250/201.1, 205, 216, 250/237 R, 239; 359/63, 66, 85; 2/8, 12, 15, 431

[56] References Cited

U.S. PATENT DOCUMENTS 4,155,122  5/1979  Budmiger ........................... 2/8
4,863,244  9/1989  Fuerthbauer et al. ............... 2/8
4,920,257  4/1990  Fuerthbauer et al. ........... 250/201.1
4,933,550  6/1990  Hegyi ............................ 250/239 X Primary Examiner—David C. Nelms
Assistant Examiner—John R. Lee
Attorney, Agent, or Firm—Tarolli, Sundheim & Covell

[57] ABSTRACT

The invention provides a light protection apparatus, particularly for welder's protective helmets, welder's protective eyeglasses or welder's protective shields. It comprises a light protection filter element, the optical transmission thereof being electrically controllable, and a control box connected to the light protection filter element to control the optical transmission of the light protection filter element. The control box comprises one or several light sensitive sensor to control the light transmission of the light protection filter element in dependence of the light falling onto the sensor or sensors, respectively. The light protection filter element is provided with shield elements adapted to shield the sensor against interfering light falling onto the sensor in at least one preselected direction.

27 Claims, 2 Drawing Sheets

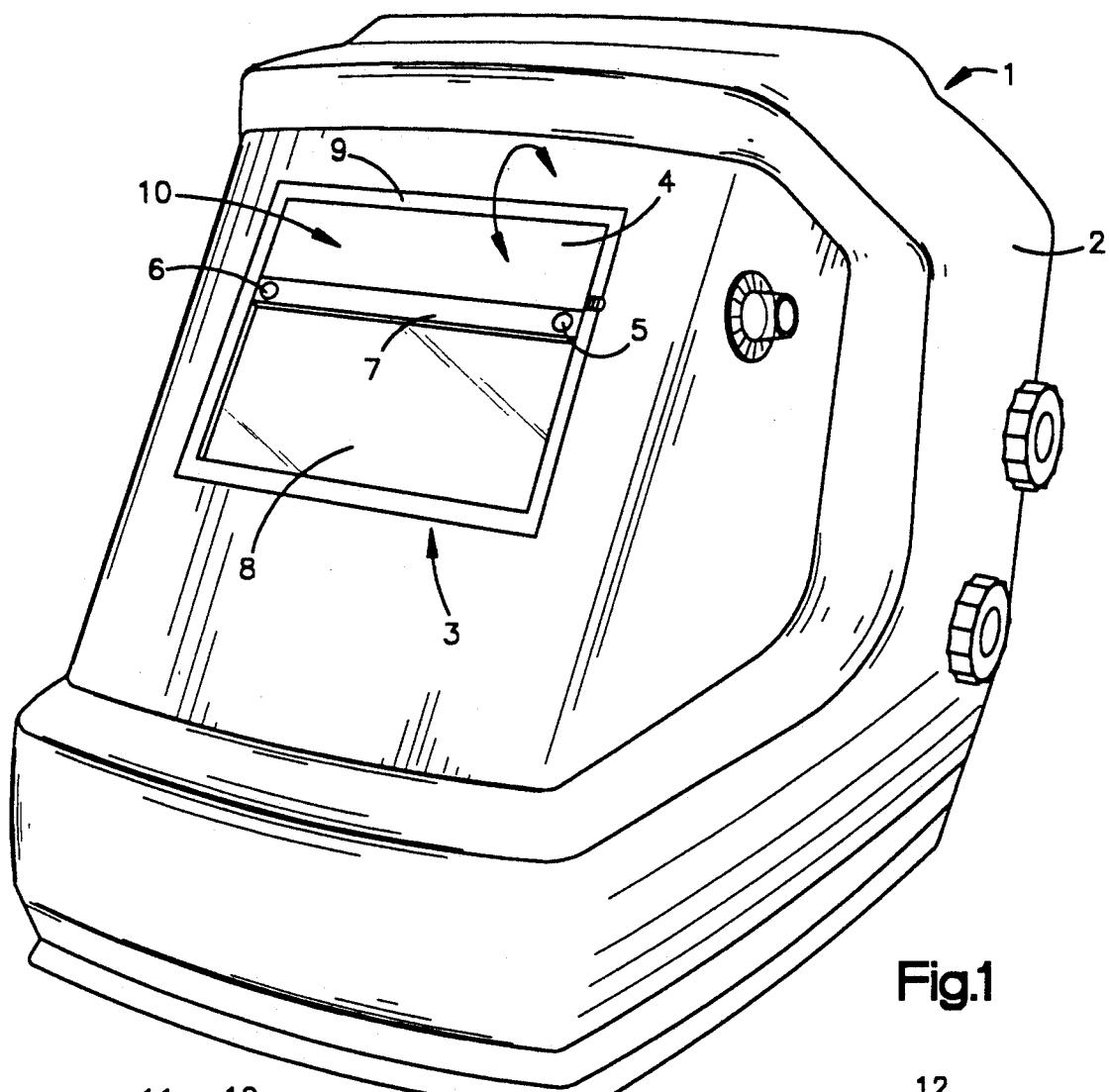
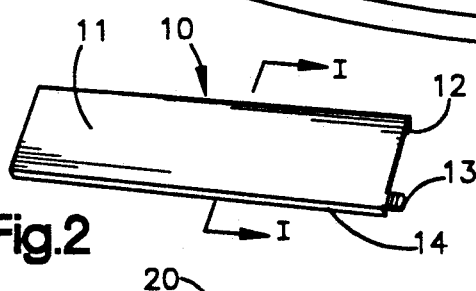
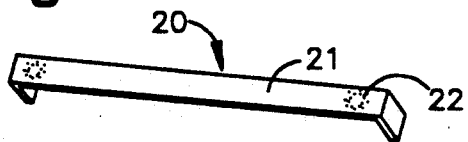
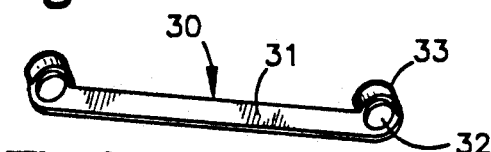
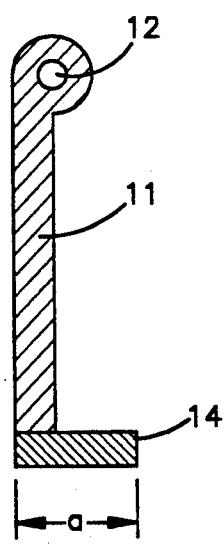

LIGHT PROTECTION APPARATUS COMPRISING AN ELECTRICALLY CONTROLLABLE LIGHT PROTECTION FILTER ELEMENT

FIELD OF THE INVENTION

The present invention refers to a light protection apparatus, particularly for welder's protective helmets, welder's protective eyeglasses or welder's protective shields, comprising a light protection filter element, the optical transmission thereof being electrically controllable. Further, the invention refers to a light shield member for a light protection apparatus, particularly for welder's protective helmets, welder's protective eyeglasses or welder's protective shields.

Prior Art

The EPO Publication No. 0,091,514—A2 and other publications disclose light protection filter elements the optical transmission characteristics thereof being electrically controllable. Particularly, these light protection filter elements make use of light sensitive sensor elements which control the transmission ratio of the light protection filter element in a manner contrary to the amount of light falling onto the light sensitive sensor.

Practice has shown that these sensors can be hit and, thereby, influenced by undesired interfering light which does not originate from the real welding operation with the result that the light protection filter element changes its transmission behaviour, particularly darkens, in an undesired moment. Known interfering light sorces are, for example, sodium vapour lamps or other similar light sources which are particularly used for the illumination of the place of work in manufacturing plants or factory buildings. This means for the user of such light protection filter elements, i.e. for the user of e.g. a welder's protective helmet, that the light sensitive sensors unwantedly react under the influence of a bright ambient illumination, particularly under the influence of the bright sodium vapour lamps used for the illumination of the place of work of a welder.

OBJECTS OF THE INVENTION

It is an object of the invention to provide a light protection apparatus, particularly for welder's protective helmets, welder's protective eyeglasses or welder's protective shields, comprising a light protection filter element, the optical transmission thereof being electrically controllable, which is designed such that interfering light coming e.g. from place of work illumination does not influence the sensor or sensors used to control the transmission of the light protection filter element.

It is a further object of the invention to provide a light shield member for a light protection apparatus, particularly for welder's protective helmets, welder's protective eyeglasses or welder's protective shields, comprising a light protection filter element, the optical transmission thereof being electrically controllable, which is designed such that interfering light coming e.g. from place of work illumination does not influence the sensor or sensors used to control the transmission of the light protection filter element.

SUMMARY OF THE INVENTION

In order to achieve these and other objects, the invention provides, according to a first aspect, a light protection apparatus, particularly for welder's protective helmets, welder's protective eyeglasses or welder's protective shields, comprising a light protection filter element, the optical transmission thereof being electrically controllable. The apparatus includes a control means connected to the light protection filter element to control the optical transmission of the light protection filter element. The control means comprises a light sensitive sensor to control the light transmission of the light protection filter element in dependence of the light falling onto the sensor. The light protection filter element is provided with shield means adapted to shield the sensor against interfering light falling onto the sensor in at least one preselected direction.

According to a second aspect of the invention, there is provided a light protection apparatus, particularly for welder's protective helmets, welder's protective eyeglasses or welder's protective shields, comprising a light protection filter element, the optical transmission thereof being electrically controllable. Again, the apparatus includes a control means connected to the light protection filter element to control the optical transmission of the light protection filter element. The control means comprises a plurality of light sensitive sensor means to control the light transmission of the light protection filter element in dependence of the light falling onto the sensors. The light protection filter element is provided with shield means adapted to shield each of said sensor means against interfering light falling onto said sensor means in at least one preselected direction.

In a first embodiment, the shield means comprises a shade means having a first transparent part and a second non-transparent part extending substantially perpendicularly to the first transparent part and running along the length of the first transparent part. The shade means is mounted to the light protection filter element in front of the sensor means such that interfering light falling onto the sensor means in at least one preselected direction is shielded.

Preferably, the shade means are pivotally connected to the light protection filter element by means of a hinge and are provided with an operating handle such that the shade means can be swivelled from an operative position to an inoperative position.

In a further embodiment, the shield means comprise a shackle member provided with light-transparent openings. Thereby, the shackle member is mounted to the light protection filter element in front of the sensor means such that the position of the openings substantially corresponds with the position of the sensor means such that interfering light falling onto the sensor means in at least one preselected direction is shielded. The openings can be partially surrounded by shielding cap members. Another possibility is to provide the shackle member with light-transparent, obliquely and/or vertically and/or horizontally running apertures.

According to a second aspect of the invention, there is provided a light shield member for a light protection apparatus, particularly for welder's protective helmets, welder's protective eyeglasses or welder's protective shields, such light protection apparatus comprising a light protection filter element, the optical transmission thereof being electrically controllable. The light protection apparatus comprises a control means connected to the light protection filter element to control the optical transmission of the light protection filter element. The control means comprises at least one light sensitive sensor to control the light transmission of the light protection filter element in dependence of the light falling onto the sensor or sensors, respectively. The light shield member comprises an elongated strip member having at least on bore, said strip member being mounted to the light protection filter element in front of the sensor or sensors, respectively, such that the position of the bore or bores substantially corresponds with the position of the sensor or sensors such that interfering light falling onto the sensor or sensors in at least one preselected direction is shielded.

BRIEF DESCRIPTION OF THE DRAWINGS

In the following, some embodiments of the invention will be further described, with reference to the attached drawings, in which:

FIG. 1 shows a perspective view of a welder's protective helmet with a built-in light protection filter element;

FIG. 2 shows a perspective view of a first embodiment of a shielding member;

FIG. 2a shows a cross sectional view of the shielding member according to FIG. 2 along the line I—I;

FIG. 3 shows a perspective view of a second embodiment of a shielding member;

FIG. 4 shows a perspective view of a third embodiment of a shielding member;

FIG. 7c shows a cross sectional view along the line A—A in FIG. 7a;

FIG. 8c shows a cross sectional view along the line B—B in FIG. 8a;

DETAILED DESCRIPTION OF SOME PREFERRED EMBODIMENTS

Figure 5:
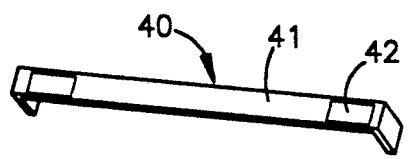
FIG. 5 shows a perspective view of a fourth embodiment of a shielding member.

FIG. 1 shows a welder's protective helmet 1 with a built-in light protective filter element 3. As is well known in the art, the light transmission ratio of such a light protective filter element is electrically controllable. Particularly, the welder's protective helmet 1 shown in FIG. 1 comprises the helmet housing 2, a light protection cassette 9, an opto-electric transducer element 4, a bridge member 7, two sensor elements 5 and 6 as well as the real light protection filter element 8.

FIG. 2 shows a first embodiment of a shielding member 10, comprising a light transparent cover 11, a hinge member 12 which serves in this example for pivotally connecting the shielding member 10 to the light protection filter member, an operating handle 13 to swivel the shielding member from an operative position to an inoperative position, as well as a non-transparent part 14 which serves, in this example, as the shielding member to prevent interfering light to reach the sensor elements 5 and 6.

FIG. 3 shows a second embodiment of a shielding member 20, comprising shackle member 21 having apertures 22 provided in the region of the outer ends of the shackle member 21. The distance between the apertures 22 and their position corresponds to the distance between and to the position of the sensor elements 5 and 6 provided on the bridge member 7 of the light protection cassette 9. The apertures 22 are designed such that they let pass light only under a certain predetermined angle with the result that interfering light is prevented to fall onto the light sensor elements 5 and 6. Preferably, the apertures 22 are in the form of bores which are designed such that they are not directed perpendicularly to the surface of the shackle member 21, but include a certain angle. With other words, the central axis of the bores include a certain angle with the central optical axis of the related sensor member, preferably downwardly directed.

FIG. 4 shows a third embodiment of a shielding member 30, comprising a shackle member 31 having apertures 22 provided in the region of the outer ends of the shackle member 21. The distance between the apertures 32 and their position corresponds to the distance between and to the position of the sensor elements 5 and 6 provided on the bridge member 7 of the light protection cassette 9. The apertures 32 are designed such that they let pass light only under a certain predetermined angle with the result that interfering light is prevented to fall onto the light sensor elements 5 and 6. To assist this effect, the apertures are provided with shielding cap members 33 at least partially surrounding said apertures 32. Thus, interfering light coming from a certain direction is prevented to fall onto the sensor elements 5 and 6.

FIG. 5 shows a fourth embodiment of a shielding member 40, comprising a shackle member 41 having apertures 42 provided in the region of the outer ends of the shackle member 41. The distance between the apertures 42 and their position corresponds to the distance between and to the position of the sensor elements 5 and 6 provided on the bridge member 7 of the light protection cassette 9. The apertures 42 are designed such that they let pas light only under a certain predetermined angle with the result that interfering light is prevented to fall onto the light sensor elements 5 and 6.

Figure 5A:
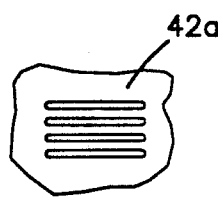
FIG. 5a shows, in an enlarged view, a first embodiment of the light transparent apertures in the shielding member according to FIG. 5.
Figure 5B:
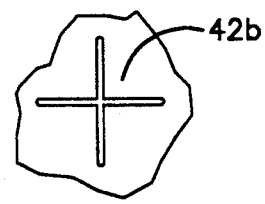
FIG. 5b shows, in an enlarged view, a second embodiment of the light transparent apertures in the shielding member according to FIG. 5.

FIGS. 5a and 5b show, in an enlarged scale, two of several variants of the design of the light transparent apertures 42. The variant shown in FIG. 5a comprises a plurality of horizontally extending slits 42a while the variant shown in FIG. 5b comprises one horizontally extending and one vertically extending slit. The particular design depends on the situation where the welder's helmet, mask or shield is used and it is possible to have realized another slit pattern, e.g. including obliquely running slits (not shown).

Figure 6:
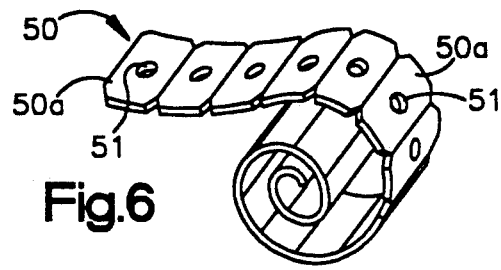
FIG. 6 shows a perspective view of a fifth embodiment of a shielding member.

FIG. 6 shows a fifth embodiment of a shielding member 50, comprising a plate member 50a the center of which is equipped with a bore 51. The plate member 50a is mounted in front of the one sensor element 5 or 6 such that the center of the bore 51 corresponds with the central axis of the sensor element 5 or 6. In this case as well, the bores 51 can be arranged under a certain angle different from the perpendicular line with reference to the surface of the plate member 50a.

Figure 7A:
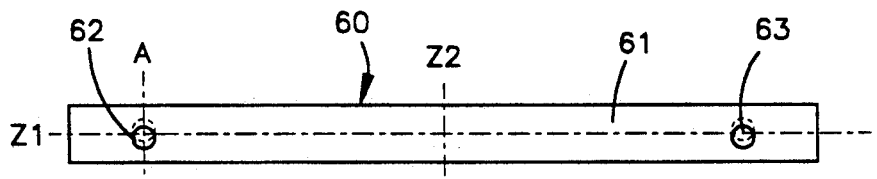
FIG. 7a shows a front view of a sixth embodiment of a shielding member.
Figure 7C:
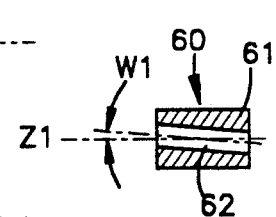
Figure 7B:
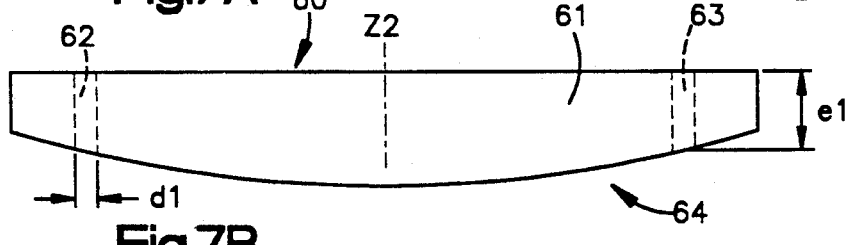
FIG. 7b shows a top view of the sixth embodiment of a shielding member.

FIGS. 7a to 7c show a sixth embodiment of a shielding member 60, comprising an elongated strip member 61 being equipped with two bores 62 and 63. Z1 designates a first central symmetry plane, running in the longitudinal extension of the strip member 61 and parallel to the even, flat top surface and lower surface of the strip member 61. Z2 designates a second central symmetry plane, running in the centre of the strip member 61 and parallel to the even, flat side surfaces of the strip member 61. The curved front surface 64 of the strip member 61 does not have any functional meaning and serves only for the purpose of improving the aesthetical appearance of the light protection filter 3.

In FIG. 7b, the strip member 61 is shown in outline. The reference d1 means the diameter of the bores 62 and 63, and the reference e1 means the thickness of the strip member 61 in the region of the bores 62 and 63. Thus, from this drawing figure, it can be seen that the bores 62 and 63 are parallel with the central symmetry plane Z2.

In FIG. 7c, the strip member 61 is shown in a cross sectional view along the line A—A (c. FIG. 7a). From this figure, it can be clarly seen that the axes of the bores 62 and 63 include an angle W1 with the central symmetry plane Z2. The result is that the sensor elements 5 and 6 arranged behind the bores 62 and 63 of the strip member 61 receive only light which essentially falls onto the sensors 5 and 6 under the aforementioned angle W1, as compared to the horizontal plane. The total amount of the light falling onto the sensors 5 and 6 arranged behind the bores 62 and 63 of the strip member 61 can be adjusted or preselected by the diameter d1 of the bores and the thickness e1 of the strip member 61.

Figure 8A:
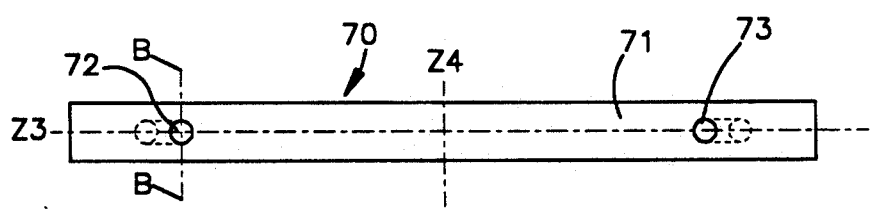
FIG. 8a shows a front view of a seventh embodiment of a shielding member.
Figure 8C:
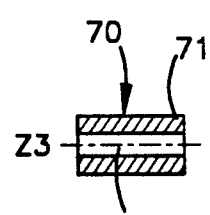
Figure 8B:
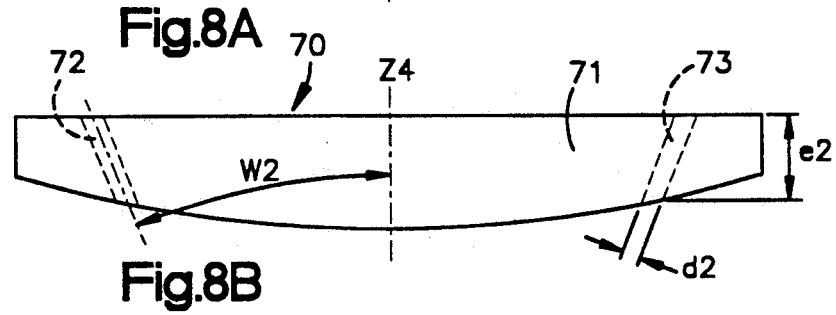
FIG. 8b shows a top view of the seventh embodiment of a shielding member.

FIGS. 8a to 8c show a seventh embodiment of a shielding member 70, comprising an elongated strip member 71 being equipped with two bores 72 and 73. Generally, the strip member 71 corresponds to the strip member 61 shown in FIGS. 7a to 7c. Z3 designates a first central symmetry plane, running in the longitudinal extension of the strip member 71 and parallel to the even, flat top surface and lower surface of the strip member 71. Z4 designates a second central symmetry plane, running in the centre of the strip member 71 and parallel to the even, flat side surfaces of the strip member 71. The curved front surface of the strip member 71 does not have any functional meaning and serves only for the purpose of improving the aesthetical appearance of the light protection filter 3.

In FIG. 8b, the strip member 71 is shown in outline. The reference d2 means the diameter of the bores 72 and 73, and the reference e2 means the thickness of the strip member 71 in the region of the bores 72 and 73. Thus, from this drawing figure, it can be seen that the axes of the bores 72 and 73 include an angle W2 with the central symmetry plane Z2.

In FIG. 8c, the strip member 71 is shown in a cross sectional view along the line B—B (cf. FIG. 8a). From this figures, it can be clarly seen that he axes of the bores 72 and 63 run parallel with with the central symmetry plane Z4. The result is that the sensor elements 5 and 6 arranged behind the bores 72 and 73 of the strip member 71 receive only light which essentially falls onto the sensors 5 and 6 from the left and the right side. Again, the total amount of the light falling onto the sensors 5 and 6 arranged behind the bores 72 and 73 of the strip member 71 can be adjusted or preselected by the diameter d2 of the bores and the thickness e2 of the strip member 62.

It is understood that the extension of the angle of the bores, as explaines in connection with the FIGS. 7a to 7c and 8a to 8c, can be combined, i.e. the bores can be oblique in vertical as well as in horizontal direction.

The shielding means shown in FIGS. 2 to 8 can be directly formed onto the light protection cassette. However, if a welder's protective helmet, for example, has already been sold in great numbers not having these shielding means, the need can arise that these shielding means have to be mounted to the helmet at a later date. Thus, the shielding means shown in the FIGS. 2 to 8 and described hereinbefore can be designed such that they can be separately sold and mounted to the welder's helmet as needed. It is even possible for the user of the helmet to buy different sets of shielding means and to mount it to its helmet in dependence whether the interfering light comes from the top or from the side.

What is claimed is:

1. A light protection apparatus, particularly for welder's protective helmets, welder's protective eyeglasses or welder's protective shields, comprising a light protection filter element, the optical transmission thereof being electrically controllable, a control means connected to said light protection filter element to control the optical transmission of said light protection filter element, said control means comprising a plurality of light sensitive sensor means to control the light transmission of said light protection filter element in dependence of the light falling onto said sensor means, said light protection filter element being provided with shield means adapted to shield each of said sensor means against interfering light falling onto said sensor means in at least one preselected direction.

2. A light protection apparatus, particularly for welder's protective helmets, welder's protective eyeglasses or welder'protective shields, comprising a light protection filter element, the optical transmission thereof being electrically controllable, a control means connected to said light protection filter element to control the optical transmission of said light protection filter element, said control means comprising a light sensitive sensor means to control the light transmission of said light protection filter element in dependence of the light falling onto said sensor means, said light protection filter element being provided with shield means ad pated to shield said sensor means against interfering light falling onto said sensor means in at least on preselected direction.

3. A light protection apparatus according to claim 2 which said shield means comprises a shade means having a first transparent part and a second non-transparent part extending substantially perpendicularly to said first transparent part and running along the length of said first transparent part, said shade means being mounted to said light protection filter element in front of said sensor means such that interfering light falling onto said sensor means in at least one preselected direction is shielded.

4. A light protection apparatus according to claim 3 in which said shade means is pivotally connected to said light protection filter element by means of a hinge means and is provided with an operating handle such that said shade means can be swivelled from an operative position to an inoperative position.

5. A light protection apparatus according to claim 2 in which said shield means comprises a shackle member provided with light-transparent openings, said shackle member being mounted to said light protection filter element in front of said sensor means such that the position of said openings substantially corresponds with the position of said sensor means such that interfering light falling onto said sensor means in at least one preselected direction is shielded.

6. A light protection apparatus according to claim 2 in which said shield means comprises a shackle member provided with light-transparent openings, said openings being partially surrounded by shielding cap members, said shackle member being mounted to said light protection filter element in front of said sensor means such that the position of said openings substantially corresponds with the position of said sensor means such that interfering light falling onto said sensor means in at least one preselected direction is shielded.

7. A light protection apparatus according to claim 2 in which said shield means comprises a shackle member provided with light-transparent, obliquely and/or vertically and/or horizontally running apertures, said shackle member being mounted to said light protection filter element in front of said sensor means such that the position of said apertures substantially correspond with the position of said sensor means such that interfering light falling onto said sensor means in at least one preselected direction is shielded.

8. A light protection apparatus according to claim 2 in which said shield means comprises at least one plate member which is provided with a bore designed in such a way that interfering light falling onto said sensor means in at least one preselected direction is shielded when said at least one plate member is mounted to said light protection filter element in front of said sensor means such that the position of said openings substantially corresponds with the position of said sensor means.

9. A light protection apparatus according to claim 2 in which said shield means comprises an elongated strip member having at least one bore, said strip member being mounted to said light protection filter element in front of said sensor means such that the position of said bore or bores substantially corresponds with the position of said sensor means such that interfering light falling onto said sensor means in at least one preselected direction is shielded.

10. A light protection apparatus according to claim 9 in which the central axis of said at least one bore forms an angle with a central symmetry plane such that the angle of incidence of the light hitting said sensor means may be preselected.

11. A light protection apparatus according to claim 9 in which the amount of light hitting the sensor is adjusted by the diameter of said bore.

12. A light protection apparatus according to claim 9 in which the amount of light hitting the sensor is adjusted by the thickness of said strip member.

13. A light protection apparatus according to claim 2 in which said shield means is integrally formed onto said light protection filter element.

14. A light protection apparatus according to claim 2 in which said shield means is plugged onto said light protection filter element.

15. A light protection apparatus according to claim 2 in which said shield means is clamped onto said light protection filter element.

16. A light protection apparatus according to claim 2 in which said shield means is removably connected to said light protection filter element.

17. A light protection apparatus according to claim 2 in which said shield means is glued onto said light protection filter element.

18. A light protection apparatus according to claim 5 in which the central axis of said bores and openings, respectively, includes an angle to the axis running perpendicular to the surface of said shackle member and said plate member, respectively, such that the angle of incidence of the light falling onto said sensor means is limited to a preselected direction.

19. A light protection apparatus according to claim 7 in which the central axis of said apertures include an angle to the axis running perpendicular to the surface of said shackle member such that the angle of incidence of the light falling onto said sensor means is limited to a preselected direction.

20. A light protection apparatus according to claim 3 in which the angle of incidence of the light falling onto said sensor means is set by the width of said second non-transparent part of said shade means.

21. A light protection apparatus according to claim 2 in which said shield means is designed such that said sensor means is shielded against interfering light substantially coming from the top.

22. A light protection apparatus according to claim 2 in which said shield means is designed such that said sensor means is shielded against interfering light falling onto said sensor means under an angle of not more than 90 degrees, with reference to the optical axis to said sensor means, seen from the top if said light protection apparatus is in normal operative position.

23. A light shield member for a light protection apparatus, particularly for welder's protective helmets, welder's protective eyeglasses or welder's protective shields, said light protection apparatus comprising a light protection filter element, the optical transmission thereof being electrically controllable a control means connected to said light protection filter element to control the optical transmission of said light protection filter element, said control means comprising a light sensitive sensor to control the light transmission of said light protection filter element in dependence of the light falling onto said sensor, said light shield member comprising an elongated strip member having at least one bore, said strip member being mounted to said light protection filter element in front of said sensor means such that the position of said bore or bores substantially corresponds with the position of said sensor means such that interfering light falling onto said sensor means in at least one preselected direction is shielded.

24. A light shield member according to claim 23 in which the central axis of said at least one bore forms an angle with a central symmetry plane such that the angle of incidence of the light hitting the sensor may be preselected.

25. A light shield member according to claim 24 in which the amount of light hitting the sensor is adjusted by the diameter of said bore.

26. A light shield member according to claim 23 in which the amount of light hitting the sensor is adjusted by the thickness of said strip member.

27. A light shield member according to claim 23 in which said light shield member is adapted to be mounted to said light protection filter element by clipping-on, by gluing or by clamping.

* * * * *

UNITED STATES PATENT AND TRADEMARK OFFICE
CERTIFICATE OF CORRECTION

| | |
|---|---|
| PATENT NO. | : 5,302,815 |
| APPLICATION NO. | : 07/936900 |
| DATED | : April 12, 1994 |
| INVENTOR(S) | : André M. Eggenschwiler |

It is certified that error appears in the above-identified patent and that said Letters Patent is hereby corrected as shown below:

Column 1, line 32, change "sorces" to --sources--.

Column 3, line 3, change "on" to --one--;
            line 48, change "8$a$;" to --8$a$.--.

Column 4, line 45, change "pas" to --pass--.

Column 5, line 21, change "clarly" to --clearly--;
            line 56, change "clarly" to --clearly-- and change "he" to --the--;
            line 57, delete "with" (second occurrence);
            line 68, change "explaines" to --explained--.

Column 6, lines 43-44, change "adpated" to --adapted--;
            line 45, change "at least on" to --at least one--;
            line 48, before "which" insert --in--.

Column 7, line 20, change "correspond" to --corresponds--.

Column 8, line 11, change "Alight" to --A light--;
            line 37, change "controllable" to --controllable,--.

Signed and Sealed this

Fifteenth Day of September, 2009

David J. Kappos
*Director of the United States Patent and Trademark Office*